United States Patent [19]

Reid, Sr.

[11] 4,198,834
[45] Apr. 22, 1980

[54] ELASTIC STOCKING WITH CIRCUMFERENTIALLY ADJUSTABLE UPPER THIGH

[75] Inventor: Lawrence G. Reid, Sr., Winston-Salem, N.C.

[73] Assignee: Carolon Company, Winston-Salem, N.C.

[21] Appl. No.: 906,023

[22] Filed: May 15, 1978

[51] Int. Cl.² .......................... D04B 9/52; D04B 9/54
[52] U.S. Cl. .................................. 66/172 E; 66/178 A
[58] Field of Search ................ 66/172 R, 172 E, 173, 66/178 A, 180, 181, 200; 2/240

[56] References Cited

U.S. PATENT DOCUMENTS

| | | | |
|---|---|---|---|
| 340,132 | 4/1886 | Loesner et al. | 2/240 |
| 2,008,936 | 7/1935 | Tait | 2/240 |
| 2,414,424 | 1/1947 | Stevens, Jr. | 66/172 R X |
| 2,702,998 | 3/1955 | Purcell | 66/178 A |
| 3,184,930 | 5/1965 | Breitinger | 66/200 |
| 3,492,675 | 2/1970 | Saltiel | 2/240 |
| 3,501,774 | 3/1970 | Norman | 2/240 X |
| 3,728,875 | 4/1973 | Hartigan et al. | 66/172 E |
| 3,828,369 | 8/1974 | Swallow | 2/239 |
| 3,856,008 | 12/1974 | Fowler et al. | 2/240 X |
| 3,975,929 | 8/1976 | Fregeolle | 66/178 A X |
| 4,048,818 | 9/1977 | Cueman | 66/178 A X |

FOREIGN PATENT DOCUMENTS

| | | | |
|---|---|---|---|
| 306521 | 6/1918 | Fed. Rep. of Germany | 2/240 |
| 3006 | of 1883 | United Kingdom | 2/240 |
| 227970 | 1/1925 | United Kingdom | 2/240 |
| 1004454 | 9/1965 | United Kingdom | 66/200 |

*Primary Examiner*—Wm. Carter Reynolds
*Attorney, Agent, or Firm*—Bell, Seltzer, Park & Gibson

[57] ABSTRACT

Circumferential adjustment is provided in a generally wedge-shaped insert sewn into a slit extending downwardly in the upper thigh engaging portion of the elastic stocking and the insert is divided longitudinally along the medial portion to provide first and second insert panels. A strip of hooked fasteners is sewn to the free edge of one of the insert panels for holding the panels in circumferentially adjusted overlapping relationship. Spaced-apart lines of walewise extending special stitch loops are provided on the insert panels to indicate the amount of overlap of the insert panels.

6 Claims, 7 Drawing Figures

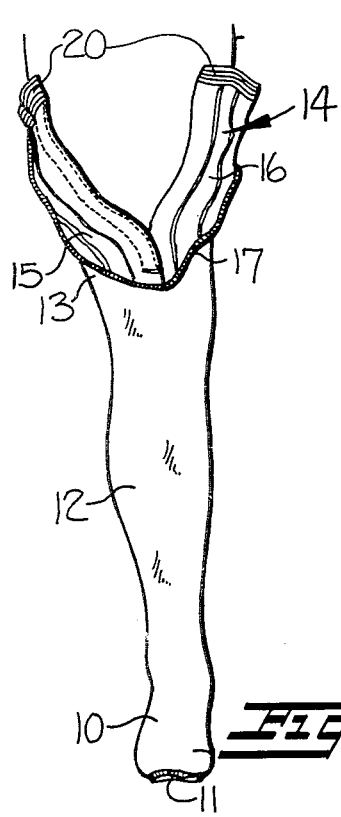
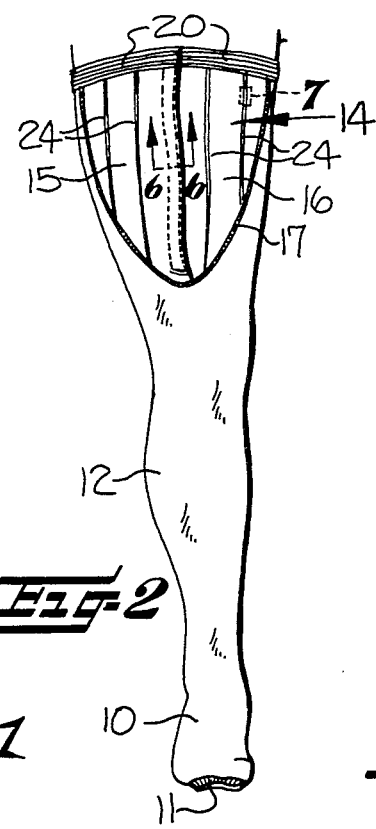
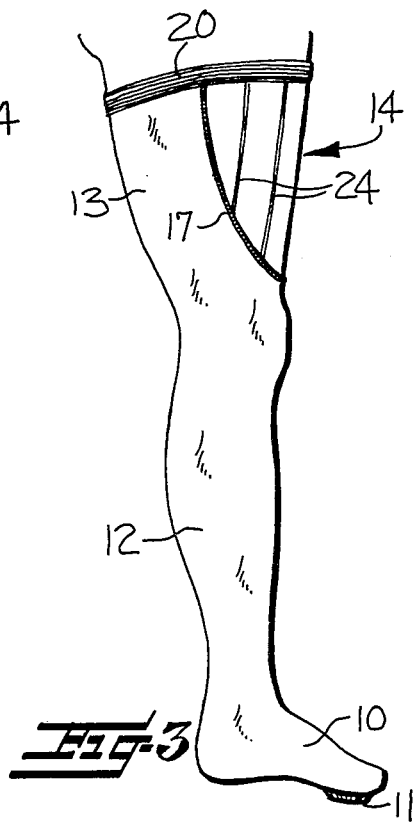
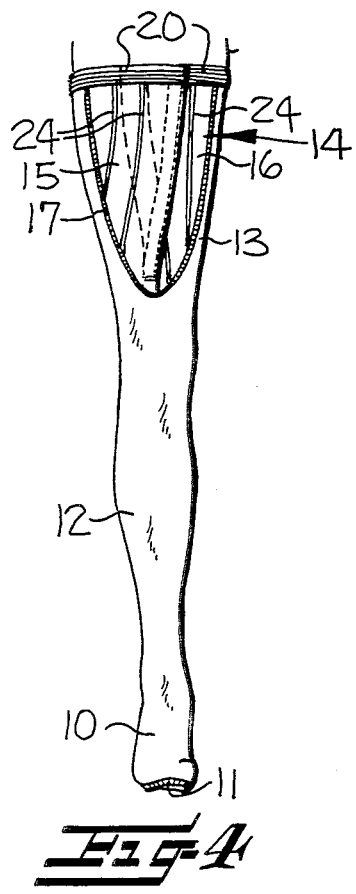
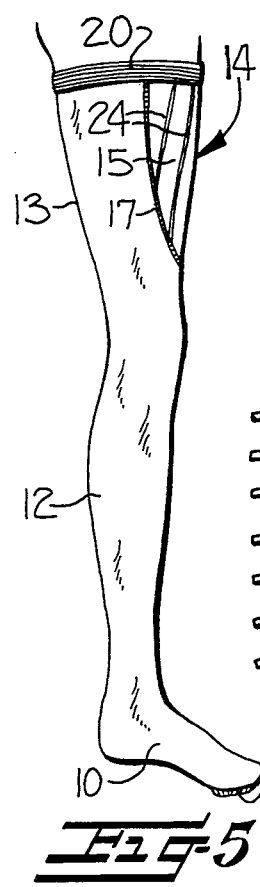
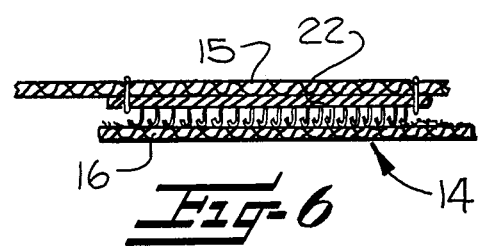
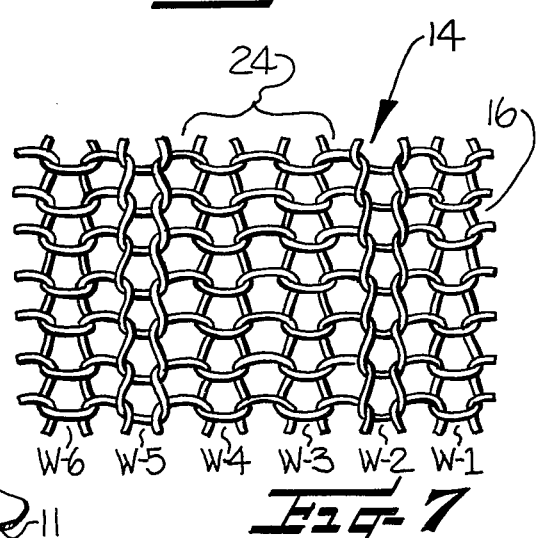

ELASTIC STOCKING WITH CIRCUMFERENTIALLY ADJUSTABLE UPPER THIGH

This invention relates generally to an elastic stocking with a circumferentially adjustable upper thigh portion and more particularly to such a stocking in which the circumferential adjustment is provided in a generally wedge-shaped insert sewn into a slit extending downwardly from the upper edge of the stocking so that the full stretchable character of the upper thigh engaging portion of the stocking is retained.

The use of anti-embolism elastic stockings on postoperative and other bedridden patients has become a fairly routine procedure. This type of stocking is adapted to exert a gradually decreasing compressive force on the leg of the wearer from the ankle to the upper thigh area and the stockings are usually manufactured in three or more different sizes which fit the normal range of leg sizes of wearers. However, in some cases, the thigh of the wearer is larger or smaller than normal so that the upper thigh portion of the stocking does not apply the proper compressive force. Also, when hip surgery is performed, the upper thigh is frequently bandaged so that the circumference is enlarged and the normal stocking will be too tight. The amount of the bandaging material used after a hip operation is sometimes reduced several days after surgery and before all bandage material is finally removed so that the circumference of the upper thigh portion of the stocking needs to be adjusted several times to maintain the proper compressive force on this portion of the patient's leg.

It is generally known to provide circumferential adjustment of the upper edge of an elastic stocking. For example, U.S. Pat. No. 3,728,875 disclosed a hook (FIGS. 4 and 5) sewn into the upper band portion for decreasing the normal circumference of the upper band portion. However, when this type of adjustment is made, it increases the compressive force in only a very narrow area which can create a tourniquet effect and interfere with blood circulation. Also, U.S. Pat. No. 3,828,369 discloses an inelastic adjustable panel sewn into a slit in the upper end of the stocking and adjacent the generally wedge-shaped insert in the upper thigh portion. However, the manufacture of this type of stocking requires that one longitudinal slit be formed for sewing in the wedge-shaped insert and another logitudinal slit be formed to attach the adjustable panel thereto. Also, the positioning of the inelastic adjustable panel adjacent the wedge-shaped insert limits and restricts the stretchability of the stretchable upper thigh portion of the stocking and the overlapping panel forms a loose tab which may irritate the patient and interfere with the bed clothing.

With the foregoing in mind, it is an object of the present invention to provide an anti-embolism elastic stocking with circumferential adjustment means provided in the generally wedge-shaped insert so that the full stretchable character of the upper thigh engaging portion of the stocking is retained. The manufacture of the present stocking requires the formation of only one slit in the upper portion of the stocking and the widthwise adjustment of the wedge-shaped insert eliminates any loose tab or flap of material.

The anti-embolism elastic stocking of the present invention includes a foot portion, a leg portion and an upper thigh engaging portion knit with stretchable yarn to provide stretch thereto and to provide a compressive force against the leg and thigh of the wearer. A generally wedge-shaped insert is sewn into a slit extending downwardly in the upper thigh engaging portion with the wider portion of the insert being positioned adjacent the upper end of the stocking. The width of the wedge-shaped insert is adjustable and is divided longitudinally along the medial portion thereto to provide first and second insert panels including adjacent free side edges. Fastening means is associated with the free edge of one of the insert panels for holding the adjacent insert panels in circumferentially adjusted overlapping relationship. The insert panels are formed of knit fabric and spaced-apart wales are formed with special stitch loops forming lines of indicia extending longitudinally of and parallel to the free side edges of the insert panels. The spaced wales of special stitch loops are provided for indicating the amount of overlap of the panels when the upper thigh engaging portion of the stocking is applied around the thigh of the wearer. Since the circumferential adjustment means is provided in the wedge-shaped insert, the full stretchable character of the upper thigh engaging portion of the stocking is retained and only one slit need be formed in the upper thigh engaging portion. Also, the fastening means is provided on the inner surface of the outer insert panel so that when the insert panels are overlapped to provide the adjustment, any surplus material remains on the inner surface of the stocking and does not interfere with wear of the stocking by the patient.

Other objects and advantages will appear as the description proceeds when taken in connection with the accompanying drawings, in which:

FIG. 1 is a front elevational view of the present elastic stocking when placed on the leg of the wearer with a relatively heavy or large upper thigh portion and with the inner free edges of the insert panels of the wedge-shaped insert being separated;

FIG. 2 is a view similar to FIG. 1 but showing the insert panels in circumferentially adjusted overlapping relationship;

FIG. 3 is a side elevational view of the stocking shown in FIG. 2;

FIG. 4 is a view similar to FIG. 2 but illustrating the stocking in position on a wearer having a relatively small or thin upper thigh and with the inner free edges of the insert panels circumferentially adjusted to overlap to a greater degree than that illustrated in FIG. 2;

FIG. 5 is a side elevational view of the stocking shown in FIG. 4;

FIG. 6 is a greatly enlarged horizontal sectional view taken substantially along the line 6—6 in FIG. 2 and illustrating the manner in which the fastening means on the free side edge of one insert panel is overlapped with and attached to the other insert panels; and FIG. 7 is a greatly enlarged fragmentary view of the area enclosed by the dotted square 7 in FIG. 2, and illustrating the special stitch loops extending walewise and forming the lines of indicia on the insert panel.

The full-length anti-embolism elastic stocking of the present invention includes a foot portion 10 which may be provided with a toe inspection opening 11 and a leg portion 12 adapted to extend upwardly above the knee of the wearer. An upper thigh engaging portion 13 extends upwardly from the leg 12 and covers the upper thigh of the wearer. Improved means for adjusting the circumferential dimension of the upper thigh engaging portion 13 is provided and comprises a generally wedge-shaped insert, broadly indicated at 14, which is sewn into a slit extending downwardly in the thigh engaging portion 13 with the wider portion of the insert being positioned adjacent the upper end of the stocking and with seamless knit fabric extending from one side of the wedge-shaped insert 14 to the other side thereof.

The insert 14 is divided longitudinally along the medial portion thereof to provide first and second insert panels 15, 16 including adjacent inner free side edges. The outer side edges of the insert panels 15, 16 are sewn into the slit in the upper thigh engaging portion along a substantially U-shaped seam line 17. An elastic tape 20 extends along and around the upper end of the stocking and has a lower edge which is stitched to the upper end of the upper thigh engaging portion 13 and to the upper ends of the first and second insert panels 15, 16. As illustrated in FIG. 1, opposite free ends of the elastic tape 20 are parallel with the inner free side edges of the first and second insert panels 15, 16.

Fastening means, illustrated as a strip of hooked fasteners 22 (FIG. 6), is sewn to the inner surface of the inner free side edge of the first insert panel 15. This strip of hooked fasteners 22 is of the well-known VELCRO type and preferably extends upwardly inside of the corresponding free end of the elastic tape 20. When the free edge of the first insert panel 15 is positioned in circumferentially adjusted overlapping relationship and pressed against the second insert panel 16, the hooked fasteners 22 grippingly engage the adjacent outer surface of the knit fabric of the second insert panel 16 and hold the wedge-shaped insert in adjusted widthwise position. The amount of overlap of the first insert panel 15, relative to the second insert panel 16, may be varied throughout the length of the generally wedge-shaped insert 14 so that there is very little overlap when worn by a patient with a large thigh, as illustrated in FIG. 2, or a greater amount of overlap is provided when worn by a patient with a relatively small thigh, as illustrated in FIG. 4.

Spaced-apart lines of indicia, indicated at 24, extend longitudinally of the insert panels 15, 16 and parallel to the free side edges. The lines of indicia 24 are provided to indicate the amount of overlap of the first insert panel 15 over the second insert panel 16 when the upper thigh engaging portion of the stocking is applied around the thigh of the wearer with the proper amount of compressive force.

As illustrated in FIG. 7, the first and second insert panels 15, 16 are knit throughout the major portions in a one-by-one rib construction so that the stitch loops face outwardly in every other wale, as illustrated in wales W-2 and W-5 of FIG. 7 and the stitch loops in the other wales face inwardly, as illustrated in wales W-1 and W-6 of FIG. 7, thereby providing a fairly smooth uniform appearance throughout the major portion of the surface of the insert panels 15, 16.

The spaced lines of indicia 24 are formed by knitting the stitch loops in a pair of adjacent wales to face inwardly, as illustrated in wales W-3 and W-4 of FIG. 7, to provide easily recognizable spaced-apart lines extending parallel to the free edge of the insert panels 15, 16. The insert panels 15, 16 are preferably knit with a nonstretchable yarn, however, the one-by-one rib knit construction permits a substantial amount of stretch in the panels 15, 16. The thigh-engaging portion 13 of the stocking adjacent the wedge-shaped insert 14 is preferably knit with courses of thermoplastic textured stretchable yarn alternating with courses of spandex yarn to provide both circumferential and longitudinal stretchability thereto.

Since the circumferentially adjustable means of the present invention is provided in the general wedge-shaped insert 14, the full stretchable character of the upper thigh engaging portion 13 of the stocking is retained and it is only necessary to form a single downwardly extending slit in the upper end of the stocking. Also, the VELCRO strip 22 is provided on the inner surface of the first panel 15 so that it overlaps and overlies the second insert panel 16 and any surplus fabric remains on the inside of the stocking where it will not irritate the patient or interfere with the bed clothing. As illustrated in FIG. 4, even when the stocking is adjusted to fit a relatively small thigh, the free end of the second insert panel 16 is positioned beneath the insert panel 15, thereby providing a relatively smooth outer surface in the area of the adjusted wedge-shaped insert 14.

In the drawings and specification there has been set forth a preferred embodiment of the invention, and although specific terms are employed, they are used in a generic and descriptive sense only and not for purposes of limitation, the scope of the invention being defined in the claims.

That which is claimed is:

1. In a full-length anti-embolism elastic stocking including a foot portion, a leg portion and an upper thigh engaging portion with an open upper end, said upper thigh engaging portion being knit with stretchable yarn to provide stretch thereto, the combination therewith of improved means for adjusting the circumferential dimension of said thigh engaging portion, said adjusting means comprising a generally wedge-shaped insert of stretchable fabric sewn into a slit extending downwardly in said thigh engaging portion with the wider portion of said insert being positioned adjacent the upper end of the stocking and with seamless knit fabric extending from one side of said wedge-shaped insert to the other side thereof, said insert being divided longitudinally along the medial portion thereof to define first and second insert panels including adjacent free side edges, fastening means attached along the inner surface of said free side edge of said first insert panel for holding said free side edge in circumferentially adjusted overlapping relationship with said second insert panel so that said free side edge of said second insert panel is positioned beneath said first insert panel to provide a relatively smooth outer surface in the area of the adjusted wedge-shaped insert, and spaced lines of indicia extending longitudinally of said second insert panel and parallel to said free side edge of said second insert, said lines of indicia indicating the amount of overlap of said first insert panel over said second insert panel when said upper thigh engaging portion of said stocking is applied in adjusted position around the thigh of the wearer so that the full stretchable character of said upper thigh engaging portion of said stocking is retained.

2. An anti-embolism stocking according to claim 1 wherein said thigh engaging portion is knit with courses of thermoplastic textured stretchable yarn alternating with courses of spandex yarn, and wherein said first and second insert panels are knit with stretchable yarn.

3. An anti-embolism stocking according to claim 2 wherein said first and second insert panels are knit throughout the major portion in a one-by-one rib stitch construction, and wherein said spaced lines of indicia comprise pairs of adjacent wales of stitch loops facing in the same direction and providing easily recognizable lines extending parallel to said free side edge of said second insert panel.

4. An anti-embolism stocking according to claim 1 wherein said fastening means comprises a strip of hooked fasteners secured to the inner surface of said free side edge of said first insert panel, said hooked fasteners being adapted to grippingly engage the adjacent outer surface of said second insert panel when said first insert panel is positioned in overlapping relationship with said second insert panel.

5. An anti-embolism stocking according to claim 1, including an elastic tape having a lower edge, stitching securing the lower edge of said elastic tape to said upper end of said upper thigh engaging portion, sitching securing the lower edge of said elastic tape to the upper ends of said first and second insert panels, and said elastic tape including opposite free ends parallel with said free side edges of said first and second insert panels.

6. An anti-embolism stocking according to claim 5 wherein said fastening means associated with said free edge of said first insert panel is also associated with the adjacent free end of said elastic tape for holding said free end of said elastic tape in overlapping relationship with the portion of said elastic tape secured to the upper end of said second insert panel.

* * * * *

UNITED STATES PATENT OFFICE
CERTIFICATE OF CORRECTION

PATENT NO. : 4,198,834
DATED : April 22, 1980
INVENTOR(S) : Lawrence G. Reid, Sr.

It is certified that error appears in the above-identified patent and that said Letters Patent are hereby corrected as shown below:

Column 1, line 37, "disclosed" should be -- discloses --.

Column 2, line 9, "thereto" should be -- thereof --.

Column 2, line 56, "panels" should be -- panel --.

Column 4, line 63, "stretchable" should be -- nonstretchable --.

Column 6, line 1, "sitching" should be -- stitching --.

Signed and Sealed this

Fifteenth Day of July 1980

[SEAL]

Attest:

SIDNEY A. DIAMOND

Attesting Officer  Commissioner of Patents and Trademarks